United States Patent [19]
Andersson

[11] Patent Number: 5,504,430
[45] Date of Patent: Apr. 2, 1996

[54] METHOD AND APPARATUS OF CONDUCTIVITY MEASUREMENT

[76] Inventor: Lars Andersson, Borje Klista Hage, S-755 92 Uppsala, Sweden

[21] Appl. No.: 267,440

[22] Filed: Jun. 29, 1994

[51] Int. Cl.$^6$ .................................................. G01N 27/02
[52] U.S. Cl. ........................................ 324/439; 324/442
[58] Field of Search .................................. 324/439, 71.1, 324/442; 204/153.1; 422/82.02, 98, 68.1

[56] References Cited

U.S. PATENT DOCUMENTS

| | | | |
|---|---|---|---|
| 3,213,361 | 10/1965 | Dornberger et al. | 324/707 |
| 3,969,669 | 7/1976 | Brault et al. | 324/442 |
| 4,160,946 | 7/1979 | Frigato | 324/442 |
| 4,808,930 | 2/1989 | Kaiser | 324/439 |
| 5,138,264 | 8/1992 | Seki et al. | 324/439 |
| 5,334,940 | 8/1994 | Blades | 324/439 |

FOREIGN PATENT DOCUMENTS

| | | | |
|---|---|---|---|
| 0684425 | 9/1979 | U.S.S.R. | 324/442 |
| 0725043 | 3/1980 | U.S.S.R. | 324/707 |
| 0815677 | 3/1981 | U.S.S.R. | 324/707 |

OTHER PUBLICATIONS

Jones et al. vol. 57 Journal of American Chemical Society Feb. 6, 1935.
Boukamp et al. Use of Low Frequency AC Measurements in Solid State Electrochemistry (From Conference) (May. 1979).
Journal of Physical Chemistry Oct. 1938 Acree et al.

*Primary Examiner*—Maura K. Regan
*Attorney, Agent, or Firm*—Young & Thompson

[57] ABSTRACT

The present invention relates to a method for measuring conductivity, in particular for use in liquid chromatography systems, and to a device for performing such measurement. In one aspect it provides a method of measuring conductivity in liquids, comprising applying an AC voltage over a conductivity measurement cell. In response to a conductance value calculated from the output of the cell, an expected frequency of the AC voltage is generated. The AC voltage frequency is set to the calculated value. The above steps are repeated until two consecutive conductance determinations differ by only a predetermined absolute value. Then the value may be displayed and registered as the true conductance value of the sample. In another aspect it provides a device for measuring conductivity in liquids, comprising a conductivity measurement cell; AC voltage means for supplying a variable AC voltage across the cell; an operational amplifier having one input connected to the AC voltage means, and the other input to the cell; an AC/DC converter connected to the output of the operational amplifier; an A/D converter connected to the output of the AC/DC converter, the output of the A/D converter being connected to a computing unit; said computing unit comprising means for calculating a conductance value based on the output from said A/D converter; means for calculating an expected AC voltage frequency from said conductance value; means for comparing said calculated expected frequency value with the frequency of the AC voltage applied across the cell; means for altering the frequency of the AC voltage supply to equal a value corresponding to the calculated conductance value if there is a difference between them; means for repeating the calculating and comparing of frequency values until the difference between actual value and expected value is below a preset absolute value; and means for displaying the conductance value.

11 Claims, 5 Drawing Sheets

METHOD AND APPARATUS OF CONDUCTIVITY MEASUREMENT

FIELD OF THE INVENTION

The present invention relates to a method for measuring conductivity, in particular for use in liquid chromatography systems, and to a device for performing such measurement.

BACKGROUND ART

Conductivity measurements on liquids are performed by applying a AC voltage across a pair of electrodes. The frequency may range from 50 Hz up to 50 kHz, depending on the electrolyte concentration in the sample. Thereby measurement errors frequently occur due to interfering phenomena at the electrodes, where a polarization effect occurs, in that ions having the same charge form layers on the electrode surfaces. This yields an additional capacitance, the so called "double-layer-capacitance". In order to minimize the influence of this interfering capacitance, one can increase the measurement frequency with increasing salt concentration.

Instruments presently available utilize a few fixed frequencies, commonly three or four, for different sensitivity ranges. Switching between the different measurement frequencies takes place automatically in dependence of the salt concentration. A disadvantage with this known method is that the various capacitances will not balance out optimally because of the limited frequency options available.

SUMMARY OF THE INVENTION

One object of the invention is to eliminate the mentioned drawback by enabling an automatic selection of optimal frequencies for each possible situation, such as varying electrolyte (i.e. salt) concentration in the samples, temperature changes etc. The invention provides a conductivity monitoring techninque with dynamics of $1 \times 10^6$ in one single measurement range, which is particularly valuable in gradient forming liquid systems.

Another object of the invention is to provide apparatus for performing such conductivity measurements.

These objects are on one hand achieved with a method of measuring conductivity in liquids, comprising applying an AC voltage over a conductivity measurement cell. In response to a conductance value calculated from the output of the cell, an expected frequency of the AC voltage is generated. The AC voltage frequency is set to the calculated value. The above steps are repeated until two consecutive conductance determinations differ by only a predetermined absolute value. Then the value may be displayed and registered as the true conductance value of the sample.

The objects are also achieved with a device for measuring conductivity in liquids, comprising a) a conductivity measurement cell; b) AC voltage means for supplying a variable AC voltage across the cell; c) an operational amplifier having one input connected to the AC voltage means, and the other input to the cell; d) an AC/DC converter connected to the output of the operational amplifier; e) an A/D converter connected to the output of the AC/DC converter, the output of the A/D converter being connected to a computing unit; said computing unit comprising 1) means for calculating a conductance value based on the output from said A/D converter; 2) means for calculating an expected AC voltage frequency from said conductance value; 3) means for comparing said calculated expected frequency value with the frequency of the AC voltage applied across the cell; 4) means for altering the frequency of the AC voltage supply to equal a value corresponding to the calculated conductance value if there is a difference between them; 5) means for repeating the calculating and comparing of frequency values until the difference between actual value and expected value is below a preset absolute value; and 6) means for displaying the conductance value.

DETAILED DESCRIPTION OF A PREFERRED EMBODIMENT AND BEST MODE OF OPERATION

Figure 1:
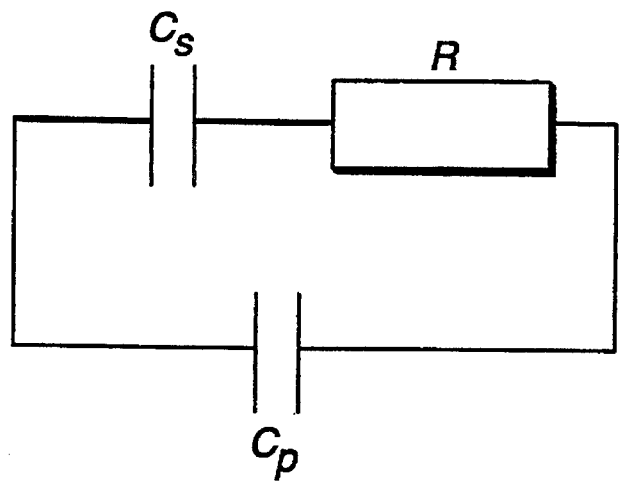
FIG. 1 shows the equivalent characteristic of a conductivity measurement cell.

In order to more easily understand the principle of the invention one should know the equivalent characteristics of the cell. The cell, shown as a simplified characteristic equivalent circuit in FIG. 1, comprises essentially three components: i) cell resistance R (the sought for conductance=1/R), ii) parallel capacitance Cp (cabling capacitance), and iii) serial capacitance Cs ("double-layer-capacitance", i.e. surfaces of contact between electrolyte and liquid).

For low conductivity values the parallel capacitance will influence the measurement, especially at higher frequencies. For high conductivity values the serial capacitance will have great influence, especially at low frequencies.

The impedance of Cp is denoted Zcp, and the impedance of Cs is denoted Zcs.

In order to be able to measure the liquid resistance (and thus also the conductance) without interfering influence of capacitances, the following relation is valid and must be met:

$$Zcs \ll R \ll Zcp$$

Thus, it is seen that for high conductance (low R), Zcs gives the largest error contribution, and in order to keep Zcs low, a high measurement frequency is required. For low conductance, Zcp contributes the most to the error, and in order to keep Zcp high, a low measurement frequency is required.

It follows that for given values of Cp and Cs there is an ideal frequency for each conductance value, where the influence of Cp and Cs cancel each other.

For the determination of optimal frequency of the AC voltage, with known values of the serial capacitance Cs, the parallel capacitance Cp, and the cell resistance R, the following relations are valid:

$$R = \frac{\left(R + \frac{1}{\omega Cs}\right) \frac{1}{\omega Cp}}{R + \frac{1}{\omega Cs} + \frac{1}{\omega Cp}} \quad (1)$$

$$R^2 + \frac{R}{\omega Cs} + \frac{R}{\omega Cp} = \frac{R}{\omega Cp} + \frac{1}{\omega^2 CsCp}$$

$$\frac{R^2 \omega Cs + R}{\omega Cs} = \frac{1}{\omega^2 CsCp}$$

$$\omega^3 R^2 Cs^2 Cp + \omega^2 RCsCp - \omega Cs = 0$$

$$\omega^2 R^2 CsCp + \omega RCp - 1 = 0$$

$$\omega = \frac{-RCp + \sqrt{R^2\ Cp^2 + 4R^2 CsCp}}{2R^2 CsCp}$$

$$\omega = \frac{-Cp + \sqrt{Cp^2 + 4CsCp}}{2CpCsR} = k_1 \frac{1}{R}$$

$$f = k_2 \frac{1}{R} = k_f \frac{k_{cell}}{R} \quad (2)$$

$$k_{cell} = 60000,\ Cp = 200pF,\ Cs = 800nF$$

$$k_f = 208.05$$

wherein
R is the cell resistance;
$\omega$ is the annular frequency (2 pf)
Cs is the serial capacitance
Cp is the parallel capacitance
f is frequency
$k_1$ is a cell dependent coefficient
$k_2$ is $k_1/(2\pi)$
$k_f$ is $k2/k_{cell}$
$k_{cell}$ is the cell dependent coefficient used to calculate the expected frequency f.

With the invention the ideal frequency is set automatically and continuously or in small increments, and thereby a true conductance will be registered in all instances. This automatic frequency setting will be explained below, but first a description of the apparatus will be given.

Figure 3:
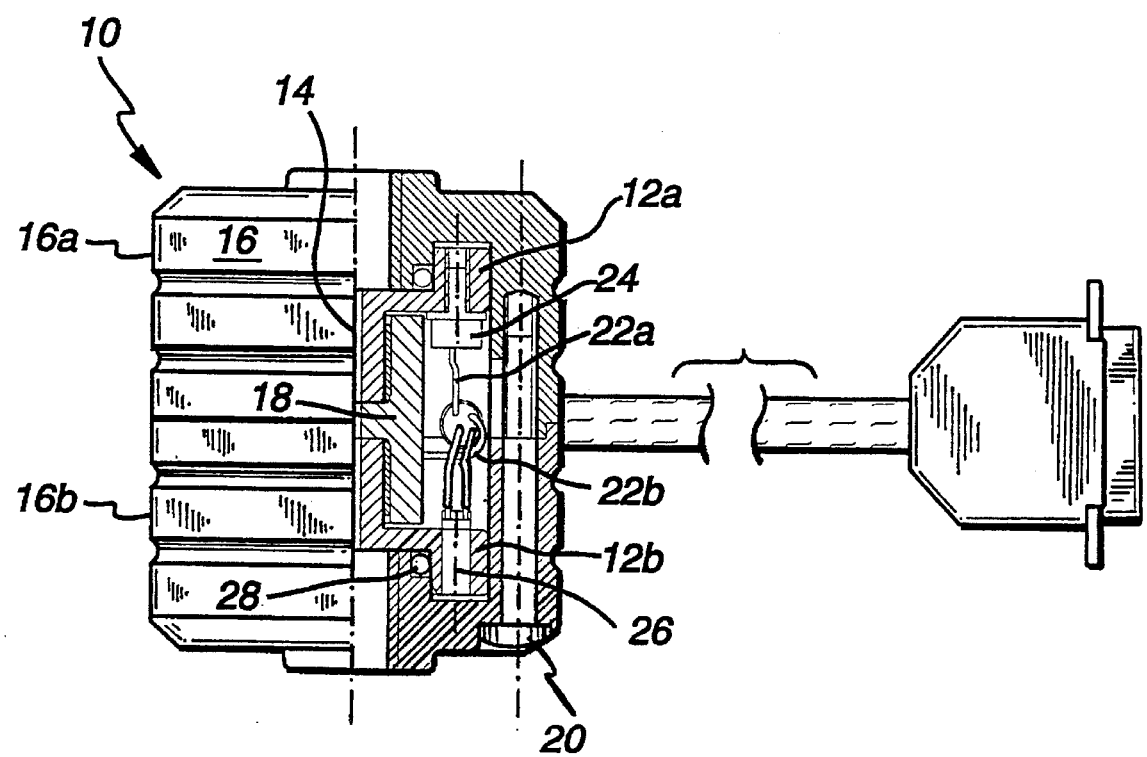
FIG. 3 shows an electrode unit partly broken away.
Figure 2:
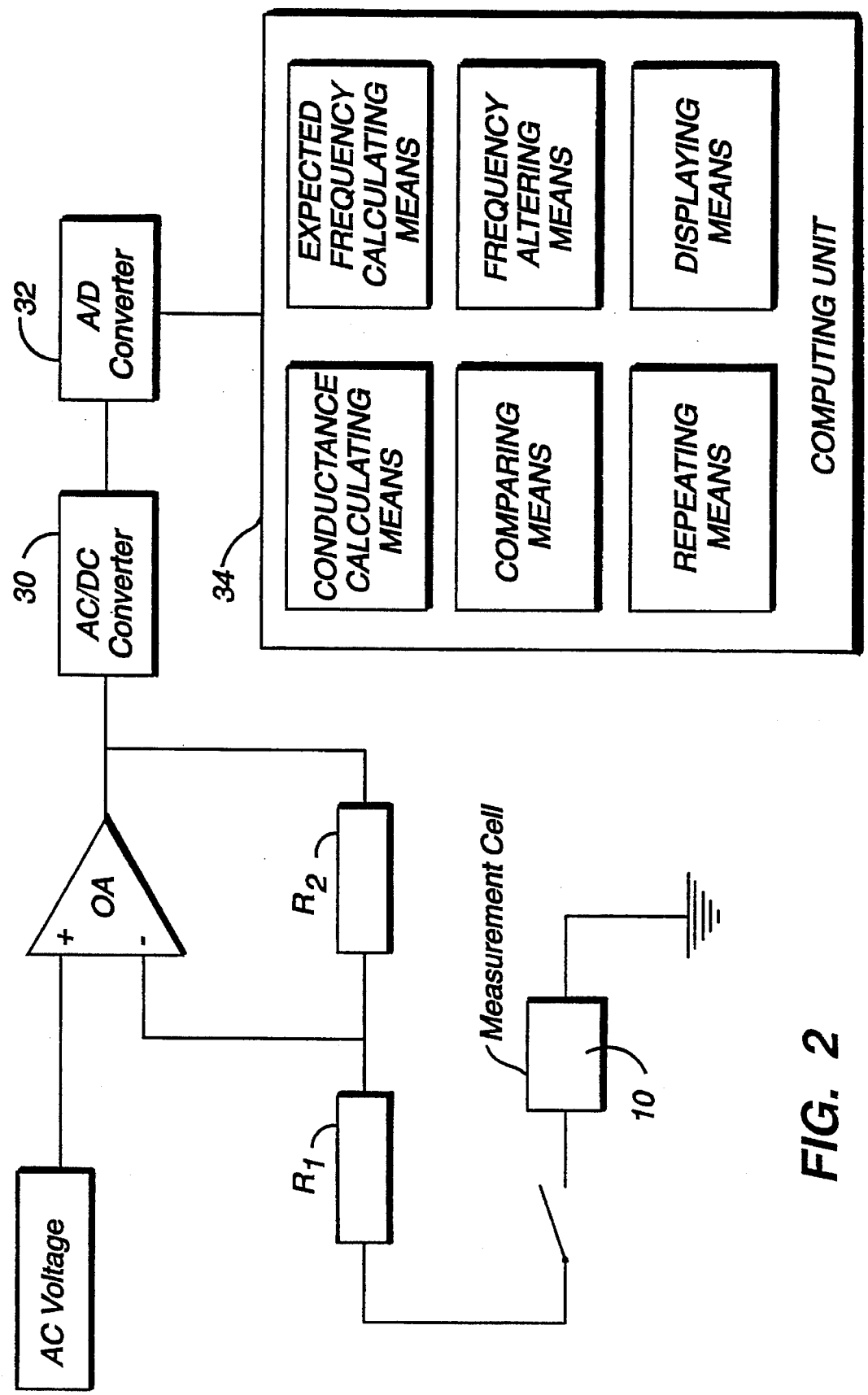
FIG. 2 shows a block representation of a measurement system.
Figure 4:
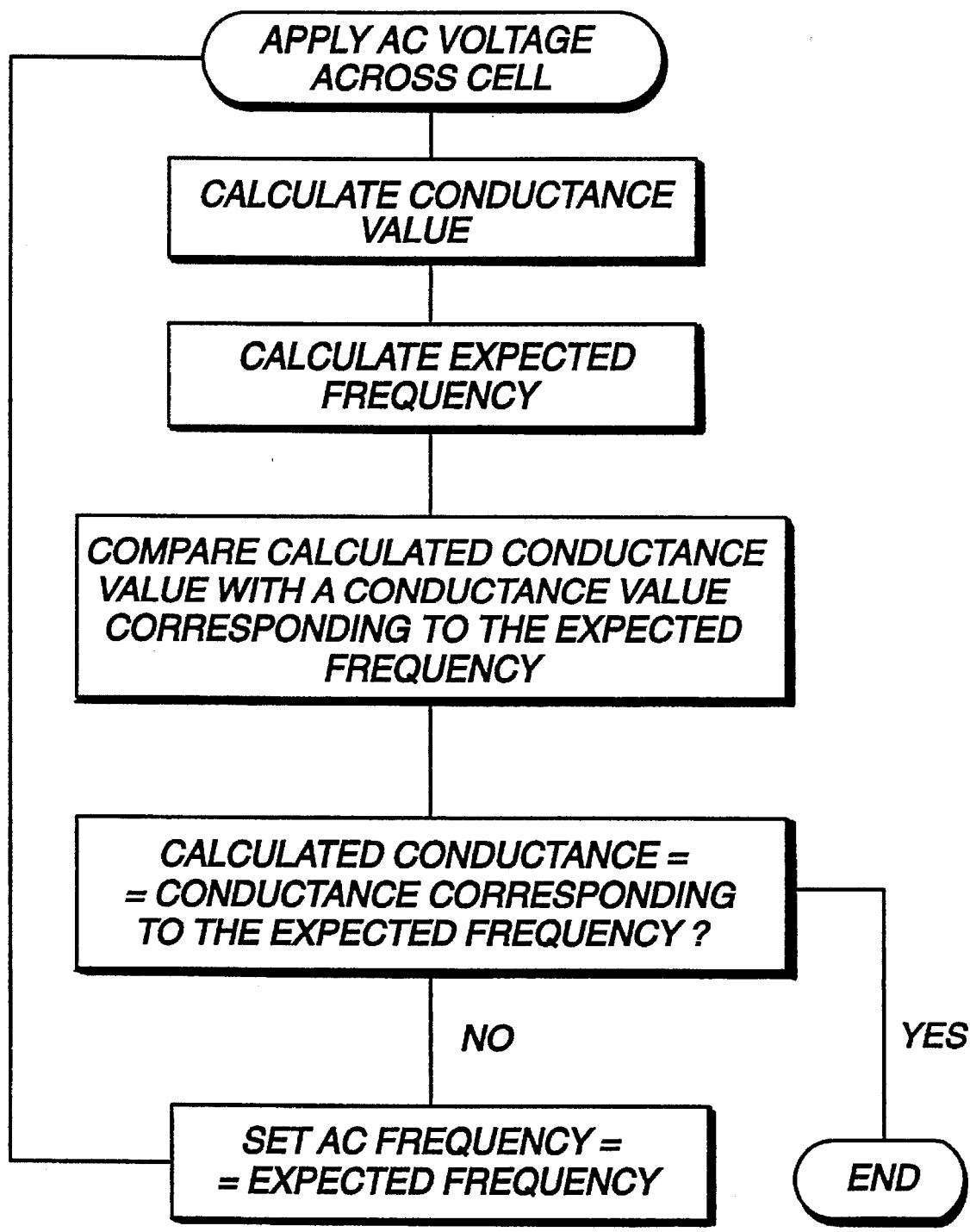
FIG. 4 is a block diagram showing the steps of the method.

A system for use in e.g. liquid chromatography is shown schematically in FIG. 2 and an electrode unit is shown in detail in FIG. 3. It should however be understood that the apparatus and method of the invention have broader utility than what is disclosed in this specific example, and is not specifically limited to liquid chromatography, but can be used for any conductivity measurement in liquids, whether flowing or stationary.

The system comprises an AC voltage source (sine wave generator) feeding an AC voltage to an Operational Amplifier OA (an example of a suitable OA is OPA606 available from BurrBrown, but the man skilled in the art could easily select appropriate units from other manufacturers). The basic electronic circuit is a non-inverting amplifier, wherein $R_1$ is connected in series with the variable cell resistance. The output of the OA is divided in two portions, the minor portion of which is applied across the cell 10.

The measurement cell 10 has two ring-shaped electrodes 12a, 12b forming a flow channel 14 for the liquid, the conductance of which is to be measured. The electrodes 12a, 12b are mounted in a housing 16 consisting of two halves 16a, 16b and kept isolated by means of a spacing element 18. The housing halves are joined by means of screws 20 (only one shown). The ring electrodes 12a, 12b extend circularly in a plane perpendicular to the plane of the drawing. The narrow flow channel 14 is formed in the center of the electrode unit along the longitudinal axis shown by the dash and dot line. The electrodes 12a, 12b are energized via cables 22a, 22b connected to the electrodes with screws 24 (only one shown). A temperature sensor 26 is mounted in the lower electrode. O-rings 28 provide leak tight sealing.

One of the electrodes is connected in series to a resistance $R_1$ (383Ω). This resistance breaks off the amplification when $R \to 0$. This enhances the dynamics of the measurement system.

$R_2$ (2 kΩ) determines the amplification of the OA. The basic functioning of the electronics is easily understood by those skilled in the art, and will not be further discussed.

The output of the OA is connected to an AC/DC converter 30. The AC/DC converter comprises a digital filter set to a notch frequency of 10 Hz. By setting the notch frequency to 10 Hz in the preferred embodiment, residual ripple from the cell is suppressed by as much as 200 dB. It also contributes to avoiding interference from the mains frequency. Again, as in the case with the incrementation of the frequency, this filter will be possible to set differently, e.g. in the case of different mains frequency. The output of the AC/DC converter 30 is fed to an A/D (Analogue-to-Digital) converter 32. The A/D converter converts the analogue output to a digital value. This value is fed to a computing unit which carries out conductance and frequency calculations (to be described). The computing unit 34 may be a microprocessor 34 which runs a program for adjusting the frequency of the AC source to optimize the measurement.

The computing unit comprises means for calculating a conductance value based on the output from said A/D converter; means for calculating an expected AC voltage frequency from said conductance value; means for comparing said calculated expected frequency value with the frequency of the AC voltage applied across the cell; means for altering the frequency of the AC voltage supply to equal the expected frequency value if there is a difference between the actual and the expected frequencies; means for repeating the calculating and comparing of frequency values until the difference between actual value and expected value is below a preset absolute value; and means for displaying the conductance value. The display means can be in the form of a digital display, which does not necessarily form part of the computing unit as such.

The measurement process is performed as follows:

An AC voltage of low initial frequency $f_i$ (e.g. 70 Hz) is applied across the electrodes. The output of the OA, appropriately converted to a digital value, is fed to the microprocessor, which calculates a conductance value by using Equation (1) above.

An expected frequency value for that conductance is calculated by using Equation (2) and the calculated frequency is compared with the initially applied frequency $f_i$ (for the purpose of this application the term "expected frequency" means the frequency that would have been expected to yield the measured and calculated conductance value, given the specific cell parameters at hand). If there is a difference between the applied and the calculated frequency, the microprocessor adjusts the applied frequency to equal the calculated frequency. A new conductance is calculated based on the output resulting from the new frequency, and Equation (2) is applied again on the new conductance value to calculate a new expected frequency. Again, the two frequencies are compared and if they differ the microprocessor again adjusts the AC voltage frequency. This procedure is repeated until the difference between the calculated frequencies lies within a small predetermined absolute range. The conductance value corresponding to the last frequency is taken as the true conductance value of the sample. In this process the frequencies are altered in increments of 10 Hz in the at present preferred embodiment. However, the selection of increment is not critical, although 10 Hz gives the advantage of avoiding interferences from the frequency of the mains voltage (50 Hz in Sweden). Obviously other selections might be possible for other mains frequencies.

The procedure may be implemented as a simple computer program.

The invention will be further illustrated by way of examples where a prior art conductance measurement system is compared with the invention.

In a typical cell as used in the Examples, the cell parameters are as indicated above, namely $$k_{cell} = 60 \text{ cm}^{-1}, Cp=200 \text{ pF}, Cs=800 \text{ nF}$$

$$k_f = 208,05 \times 10^{-3}$$

These values are cell specific and are determined for each cell by means of standard solutions with known conductance.

EXAMPLE 1

Figure 5:
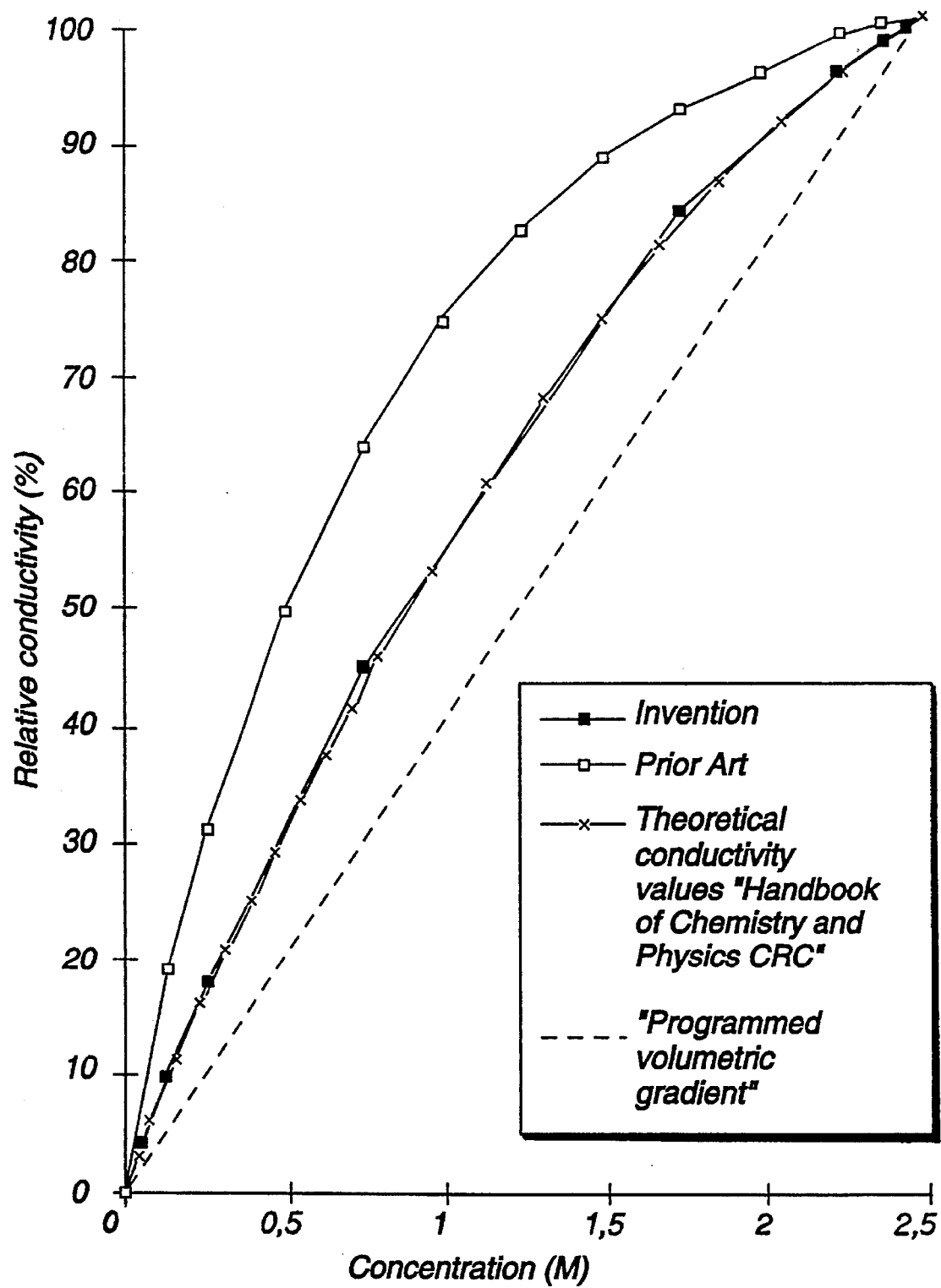
FIG. 5 is a graph showing a conductance measurement comparison between a prior art system and the invention.

For a cell having the above characteristics, conductivity measurements were carried out in a 0–2,5M gradient of $(NH_4)_2SO_4$, see FIG. 5. The gradient was provided by passing a concentrated solution through the flow channel of the cell, and continuously diluting the solution. Measurements were carried out with a prior art device and with a device and method of the invention. In the graph in FIG. 5 theoretical conductivity values are plotted in addition to measured values, and also the "programmed volumetric gradient" is also plotted. Said gradient represents an ideal situation where conductance is linearly dependent on concentration. As can be seen, the invention gives results that are very close to the theoretical values. In contrast, the prior art device exhibits strong deviation from theory.

EXAMPLE 2

Figure 6:
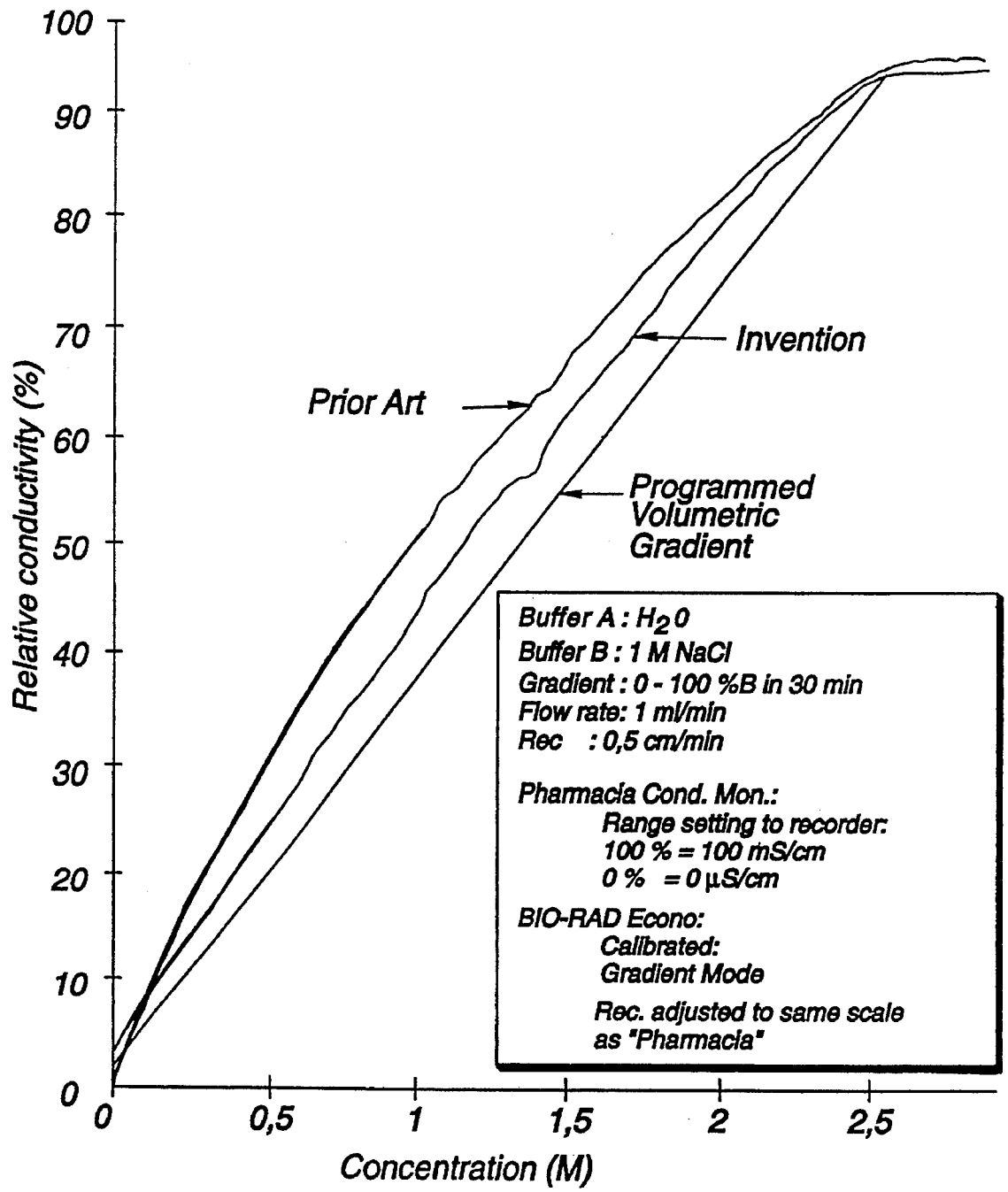
FIG. 6 is a graph showing another comparison between prior art and the invention.

The same set up as in EXAMPLE 1 was used, but the gradient was 0–1M NaCl. Also in this case a significant difference between the prior art system and the invention can be seen. The prior art overestimates the conductance values considerably (FIG. 6).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A method of measuring conductivity in liquids, comprising the following steps:
   i) applying an AC voltage over a conductivity measurement cell in contact with a sample liquid;
   ii) in response to a conductance value calculated from the output of the cell, calculating an expected frequency of the AC voltage;
   iii) setting the AC voltage frequency to the calculated value;
   iv) repeating steps ii) and iii) until two consecutive conductance determinations differ by only a predetermined absolute value.

2. The method of claim 1, comprising displaying the value from step iv) as the conductance of the sample.

3. The method of claim 1, wherein the frequency is varied in increments of 10 Hz.

4. The method of claim 1, wherein the frequency is varied between 50 Hz and 50 kHz.

5. A method of measuring conductivity in liquids, comprising the following steps:
   a) applying an AC voltage, having an initial frequency, across a pair of electrodes in contact with a sample liquid;
   b) registering the resulting current between the electrodes and determining a conductance value from said current;
   c) calculating an expected frequency of the AC voltage from said conductance value and comparing said expected frequency with said initial frequency, and in response to said comparison, setting the AC voltage to the expected frequency if there is a difference between the two;
   d) registering the current again and determining a new conductance value;
   e) repeating steps c)–d) until two consecutive conductance determinations yields the same value within a predetermined tolerance.

6. The method of claim 5, comprising displaying the value from step e) as the conductance of the sample.

7. The method of claim 5, wherein the frequency is varied in increments of 10 Hz.

8. The method of claim 5, wherein the frequency is varied between 50 Hz and 50 kHz.

9. A device for measuring conductivity in liquids, comprising
   a) a conductivity measurement cell;
   b) AC voltage means for supplying a variable AC voltage across the cell;
   c) an operational amplifier having one input connected to the AC voltage means, and the other input to the cell;
   d) an AC/DC converter connected to the output of the operational amplifier;
   e) an A/D converter connected to the output of the AC/DC converter, the output of the A/D converter being connected to a computing unit;
said computing unit comprising
   1) means for calculating a conductance value based on the output from said A/D converter;
   2) means for calculating an expected AC voltage frequency from said conductance value;
   3) means for comparing said calculated expected frequency value with the frequency of the AC voltage applied across the cell;
   4) means for altering the frequency of the AC voltage supply to equal the expected frequency value if there is a difference between the actual and the expected frequencies;
   5) means for repeating the calculating and comparing of frequency values until the difference between actual value and expected value is below a preset absolute value; and
the device further comprising means for displaying the conductance value.

10. The device of claim 9, comprising means for varying the frequency of the AC voltage continuously or in small increments.

11. Liquid chromatography system comprising a conductance measurement device as claimed in claim 10.

* * * * *